United States Patent [19]

Gersten

[11] Patent Number: 5,214,456
[45] Date of Patent: May 25, 1993

[54] MAPPING OF CORNEAL TOPOGRAPHY WITH DISPLAY OF PUPIL PERIMETER

[75] Inventor: Martin Gersten, New York, N.Y.

[73] Assignee: Computed Anatomy Incorporated

[21] Appl. No.: 774,567

[22] Filed: Oct. 9, 1991

[51] Int. Cl.$^5$ .............................................. A61B 3/10
[52] U.S. Cl. .................................... 351/212; 351/204; 351/206; 351/246
[58] Field of Search ............... 351/206, 212, 210, 204, 351/246

[56] References Cited

U.S. PATENT DOCUMENTS 4,863,260  9/1989  Gersten et al. ...................... 351/212
4,950,069  8/1990  Hutchinson ......................... 351/210

Primary Examiner—Rodney B. Bovernick
Assistant Examiner—Hung Xuan Dang
Attorney, Agent, or Firm—Howard R. Popper

[57] ABSTRACT

Method for accurately displaying the location of the pupil perimeter on a corneal topography map such as is disclosed in the prior art Gersten et al., U.S. Pat. No. 4,863,260. In the process of deriving such topographic information, the process disclosed in that patent obtained a two-dimensional video image of the cornea. In the method of the present invention, the background illumination of the video image is sampled and the video signal is corrected for the effects of camera distortions, artifacts, and specular glare. The corrected data is analyzed and the point at which the greatest rate of change in background illumination occurs is determined to be a point on the periphery of the pupil. The peripheral points so determined are then displayed in superposition to the corneal topographic map thereby indicating the pupil outline.

5 Claims, 5 Drawing Sheets

MAPPING OF CORNEAL TOPOGRAPHY WITH DISPLAY OF PUPIL PERIMETER

TECHNICAL FIELD

This invention relates to apparatus for quantitatively mapping and displaying corneal contours and more particularly to such apparatus useful in evaluating pre- and post-operative surgical procedures.

BACKGROUND OF THE INVENTION

In U.S. Pat. No. 4,863,260, apparatus is disclosed for quantitatively assessing and displaying corneal topography. The dioptric refraction exhibited over the corneal surface is shown in a color-coded display that employs a distinctive color for each fraction of a diopter present. The topographic display is obtained by illuminating the cornea with a pattern of structured light. The structured light is provided by a series of concentric rings spaced along a translucent, illuminated plastic cylinder. The apex of the patient's cornea is positioned at point at adjacent the open end of the illuminated cylinder at which two laser beams intersect. In calibrating the apparatus a series of slightly different diameter perfect spheres are positioned at the point determined by the intersection of the laser beams. The spacing of the illuminated rings in the plastic cylinder is such that the structured light pattern appearing on the perfect spheres is a series of equally spaced rings. A two-dimensional video image of the ring pattern appearing is acquired. The extent to which the structured light pattern appearing on a similarly positioned human cornea departs from the pattern exhibited by a perfect sphere is used to determine the corneal topography. The video image of the ring pattern is radially scanned and the coordinates of points which appear to lie on the rings are determined. From the two-dimensional coordinates of such points the processing apparatus constructs a model of the three-dimensional corneal surface.

Although the prior art color display provides much useful topographic information and has gained wide acceptance, the assessment of the patient's vision ultimately depends on whether the desired dioptric powers are so located as to focus an image through the pupil. Accordingly, it would be useful to provide the exact location of the pupil on the topographic display. However, the prior art apparatus, which analyzed the ring pattern appearing on the corneal surface to provide topographic data, yielded no information about the pupil since the pupil is not on the corneal surface and had nothing to do with the topography of the corneal surface being measured.

SUMMARY OF THE INVENTION

I have discovered that information about the location of the pupil can, in fact, be ascertained from the video image of the corneal surface. In accordance with the principles of the present invention, the outline of the pupil is ascertained by processing the video data. As the scanning of the video image proceeds from the apical portion of the cornea to the limbus (or across the image of a corneal meridian), the illumination level is ascertained. The illumination level turns out to be a function of the intensity levels contributed by the illuminated rings, by reflections of the eyelashes, by specular glare from the corneal surface and, since the cornea is transparent, by the iris and the remainder of the corneal background, of which the pupil is the darkest area. The intensity of the background illumination reported by the video camera therefore tends to be rather dim over the area defined by the pupil becoming increasingly brighter radially outward over the iris area.

The video data acquired by the video camera is filtered to separate the background signal from the ring signal. In accordance with my method, the radial scan point at which the greatest rate of change in background intensity occurs determines a point where the pupil meets the iris.

In the illustrative embodiment, the greatest rate of change is determined by using a "scanning window" of predetermined width to determine whether the pixel currently being scanned has a greater intensity, illustratively than any of the eight pixels to the left and to the right of the pixel being scanned. Rates of changes of illumination intensity for adjoining pixel positions are compared until the rate of change changes sign. The pupil outline is then digitally smoothed, plotted, and written to the storage disk.

BRIEF DESCRIPTION OF THE DRAWINGS

The foregoing objects and features of the invention may become more apparent from the following general description when read together with the drawings, in which.

DETAILED DESCRIPTION

Figure 1:
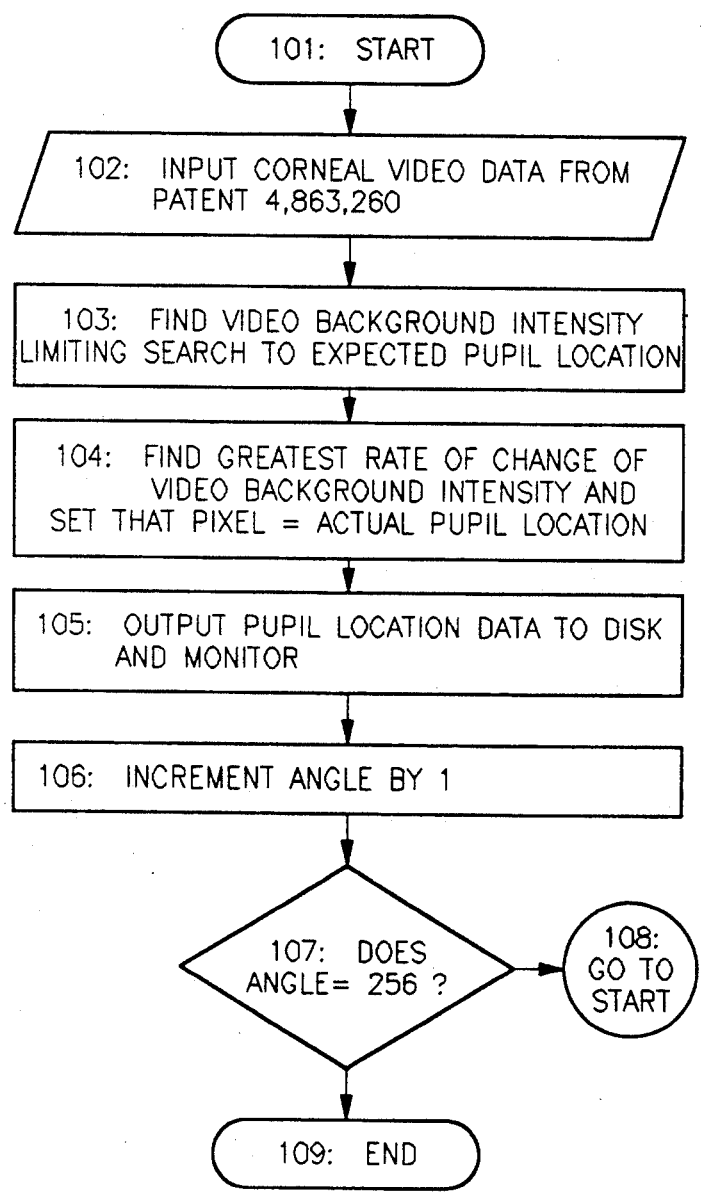
FIG. 1 is a flow chart of the principal processing steps of my invention.
Figure 2:
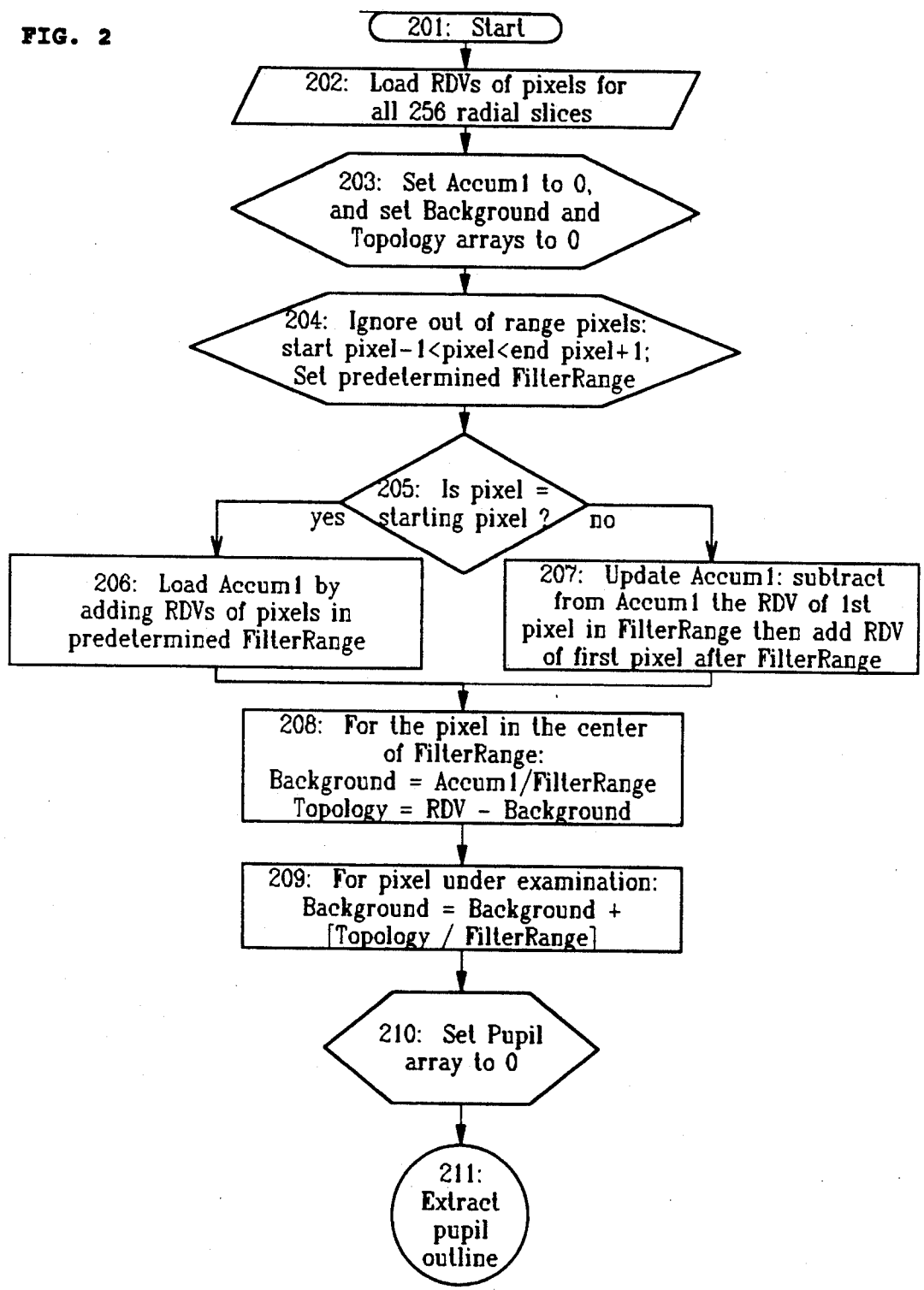
FIG. 2 is a detailed flow chart of some of the steps referred to at step numbers 103 and 104 of FIG. 1.
Figure 3:
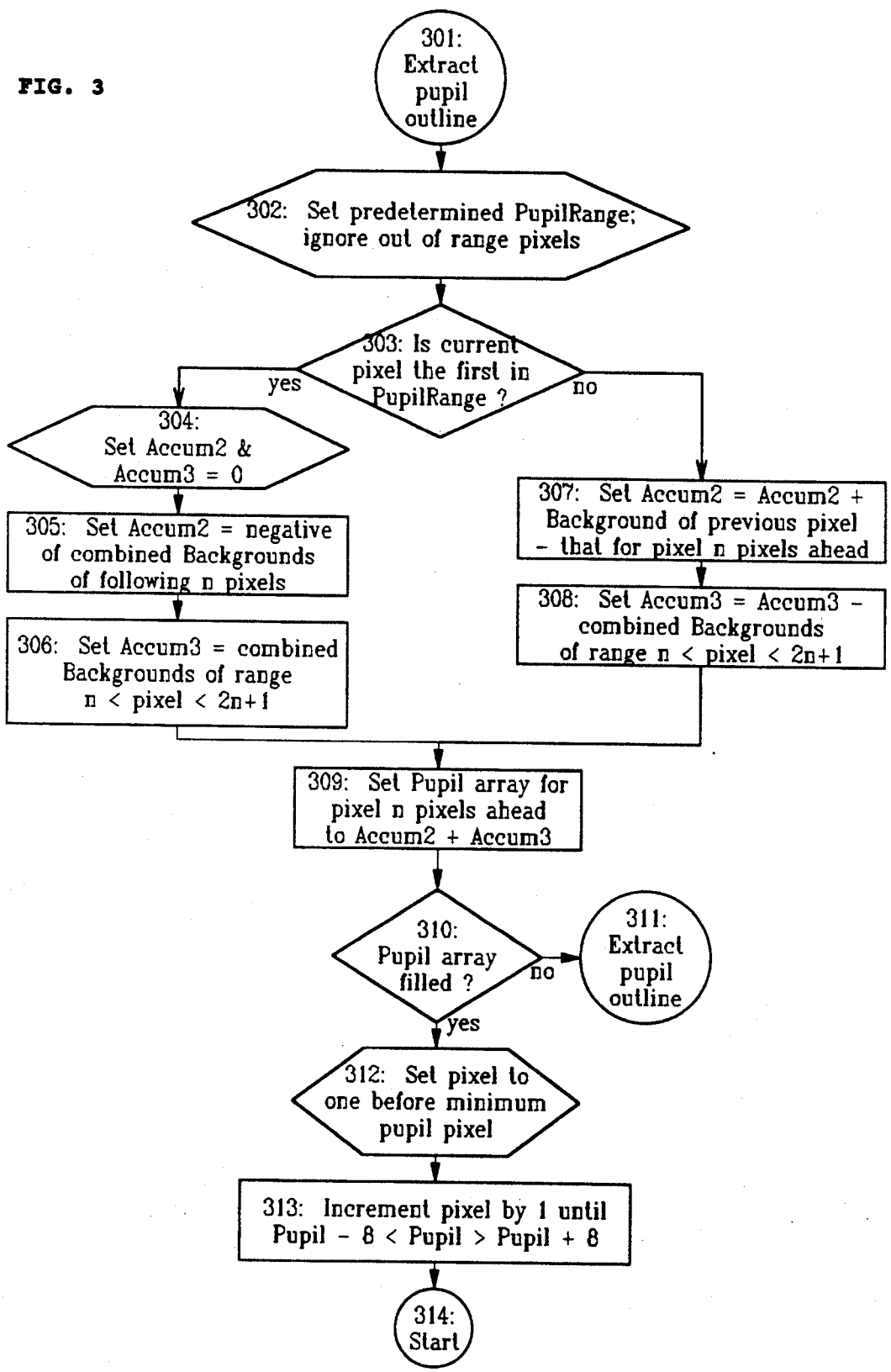
FIG. 3 is a detailed flow chart which shows the remaining processing steps of FIG. 2.

As a matter of convenience, when referring to any step in a flow chart, the number of that step will be indicated. FIG. 1, 2, and 3 use step numbers in the 100's, 200's, and 300's respectively.

Referring to FIG. 1, step 102 reads, "INPUT CORNEAL VIDEO DATA FROM U.S. PAT. NO. 4,863,260". Step 103 reads, "FIND VIDEO BACKGROUND INTENSITY LIMITING SEARCH TO EXPECTED PUPIL LOCATION". The process executed by these two is advantageously the same as that disclosed in U.S. Pat. No. 4,863,260.

Step 104 reads, "FIND GREATEST RATE OF CHANGE OF VIDEO BACKGROUND INTENSITY AND SET THAT PIXEL=ACTUAL PUPIL LOCATION". This box is the basis for FIG. 2 and FIG. 3 below.

The output of the pupil location data to display is output in step 105. In step 106 the detection angle is incremented after which step 107 determines whether all radial pupil positions, illustratively 256 in number, have been determined. If not, steps 101 through 107 are repeated.

In general, a decision is made as to where the pupil radius is expected to be located. To speed up processing, the range of locations at which the pupil is likely to occur are used in the calculations. Then, for each one of the 256 radial scans, the data obtained is examined to determine the greatest rate of change in background intensity over the expected range.

It has been determined that the greatest rate of change in background intensity occurs where the background changes from the darkness of the pupil to the relative lightness of the iris regardless of the actual iris color. Even in the case of a dark brown iris, the rate of change in background intensity is still greatest where the pupil meets the iris.

The pixel containing the greatest rate of change is found by examining eight pixels to the left and to the right of the pixel under examination. If the rate of change in background intensity varies little over this seventeen pixel range, then the pixel under examination is not the pixel containing the greatest rate of change. The next pixel is then examined and the procedure repeats itself until the rate of change is maximized. The pixel where the greatest rate of change is found is the pixel containing the location of the pupil.

Referring now to FIG. 2 and to FIG. 3, these general principles are explicitly displayed. The raw data values [called RDVs] of pixels in all 256 radial slices are loaded into an array, step 202. Pixels are picture elements or points containing a numerical value representing the average brightness of an image over the area that the pixel subtends on the original continuous image. Raw data values refer to the signal obtained by prior U.S. Pat. No. 4,863,260, represented pixel illumination intensity. Pixel illumination intensity is the intensity or brightness of the videographed subject as recorded and digitized by measuring the voltage at closely spaced intervals along each video camera scan line. An accumulator is initialized to 0 as well as two arrays, "Background" and "Topology", step 203. An accumulator is a temporary computer memory address where numbers are totaled or stored. Background refers to the background signal that is a part of the raw data value input signal. Topology refers to the other part of the raw data value input signal and, when analyzed in accordance with prior U.S. Pat. No. 4,863,260, yields the topological configuration of the corneal exterior surface. It is this background signal that contains the information yielding the pupil outline.

A range of pixels is selected contained the range of pixels for the pupil location [called PupilRange] as well as additional pixels on either side necessary for image processing; all other pixels are ignored, step 204. Then a filter range [called FilterRange] is selected, step 204. Filters are mathematical constructs that produce modified images emphasizing some aspect of the original image at the expense of others. A pixel is examined to determine if it is the first in the selected image processing range, step 205, and, if so, the first accumulator is loaded with all RDVs for pixels in FilterRange, step 206. If not, the accumulator needs not be loaded but must be updated but subtracting the value of the first pixel in FilterRange and adding the value of the first pixel after FilterRange, step 207. This would effectively "slide" the filter over the image processing range, one pixel at a time.

The image processing is continued by selecting the pixel in the center of FilterRange, and, for that pixel, setting Background equal to the average pixel illumination intensity over the filter range and solving for Topology by subtracting Background from the RDVs, step 208. Then, for the pixel currently under examination (as opposed to the one at the center of the filter), Background is set to the Background as calculated for the pixel at the center of the filter plus the Topology divided by the number of pixels in FilterRange, step 209. An array contained data regarding pupil outline [called, Pupil] initialized to 0, step 210, and the pupil outline is extracted from Background, steps 211 and 301.

A range of pixels over which the pupil can be selected is determined [called, PupilRange] and all out of range pixels are ignored, step 302. A pixel is examined to determine if it is the first in PupilRange, step 303, and, if so, a second and third accumulator are initialized, step 304, the second accumulator is set to the negative of the combined Backgrounds of n pixels, step 305, and the third accumulator is set to the combined Backgrounds of the following n pixels, step 306. If not, the second accumulator has added to itself the Background of the previous pixel minus that of the pixel n pixels ahead, step 307, and the third accumulator subtracts from itself the combined Backgrounds of the n pixels following the first set of n pixels, step 308.

Finally, the array Pupil is set for the pixel n pixels ahead of the current pixel to the combined values of the second and third accumulators, step 309. If Pupil is not yet filled for all 256 slices, step 310, the procedure loops back until it is, step 311. If it is filled, it is then analyzed in the PupilRange, step 312, for greatest rate of change in background intensity by incrementing the search pixel by pixel unto the value in Pupil for the pixel under evaluation is greater than the values in Pupil for the pixels eight pixels to the left and right, step 313. This pixel representing the greatest rate of change in background intensity identifies the pupil position. The entire process repeats itself should another exam be required, step 314.

Figure 4:
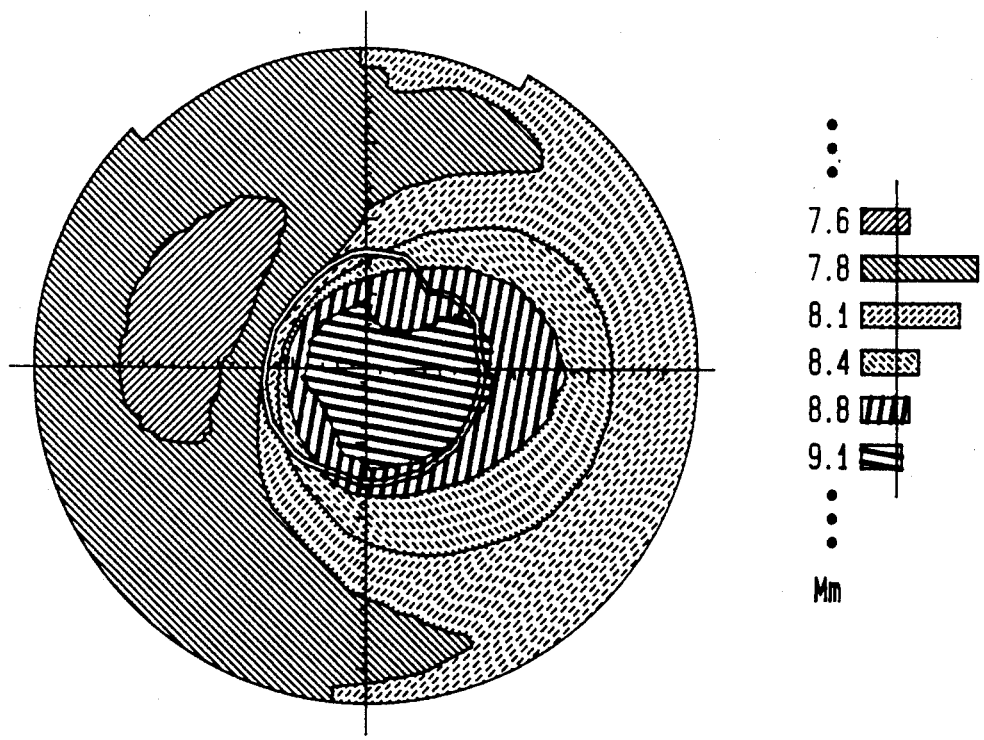
FIG. 4 is a photograph of an image of the pupil outline data acquired by my method in which the pupil outline appears as an asymmetric white circle superimposed on a color may of the corneal topography.

Referring to FIG. 4, the data appears as an asymmetric ring (unless the pupil is perfectly symmetrical) superimposed on the output already disclosed by the '260 patent. The '260 output is, mainly, a color scale map of dioptric powers of the cornea. No pupil location is shown. Now, in accordance with my invention, the location of the pupil is precisely calculated and reflected on the color scale corneal map. This precise location of the pupil, manifested by the asymmetrical white ring on the color scale, is intended to enhance an ophthalmic surgeon's ability to correctly decide upon an appropriate course of action.

Figure 5:
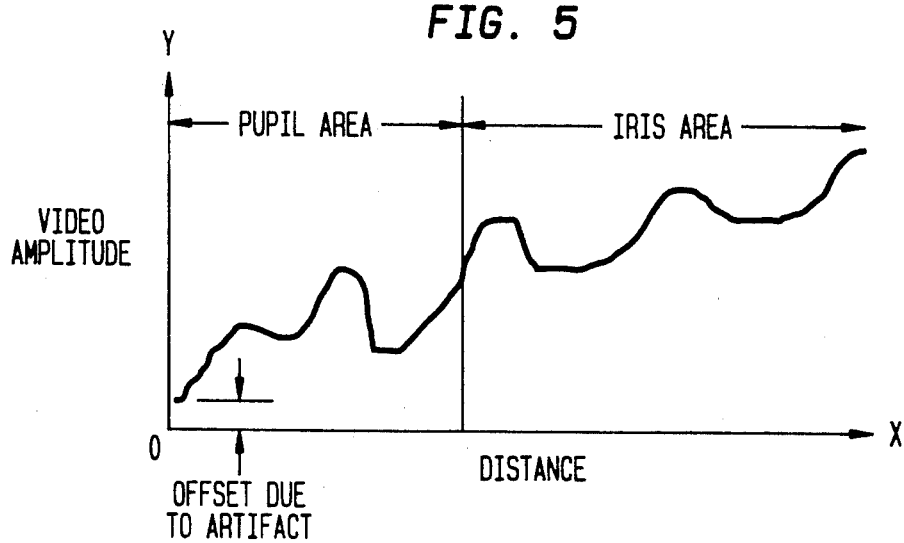
FIG. 5 depicts the raw data as collected by the video camera.

Referring now to FIG. 5, the graph plots distance from the center of the eye versus video amplitude of the signal received as disclosed by patent no. '260. In the '260 patent, the signal's background intensity is zeroed out and discarded as unused information. The present invention utilizes this background signal which contains information necessary to find the pupil outline. FIG. 5 is a graph of the raw data before this invention begins its major tasks.

Figure 6:
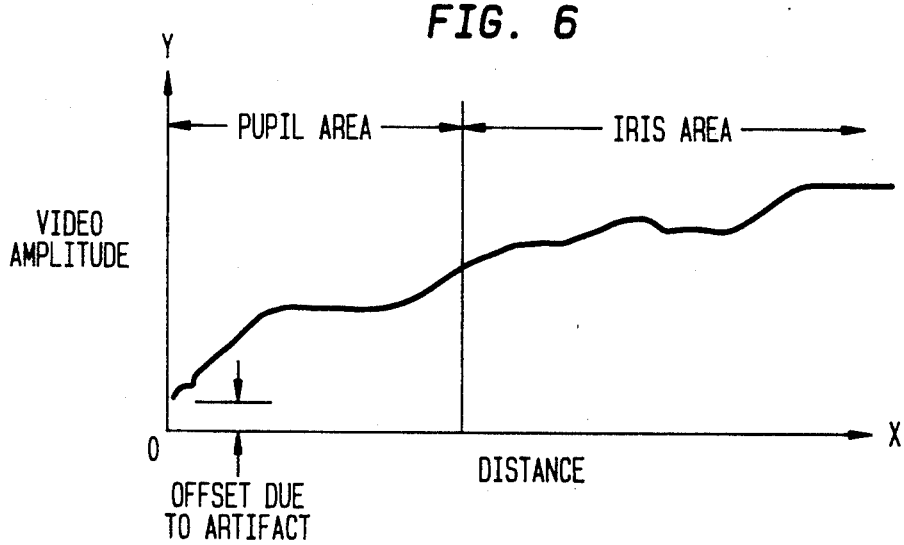
FIG. 6 depicts the low pass filtered raw data.

Referring now to FIG. 6, the graph plots the raw data as it appears after it has been low pass filtered. The low pass filtering separates the background signal from the raw data. It is this signal that is analyzed for the said maximum rate of change.

Figure 7:
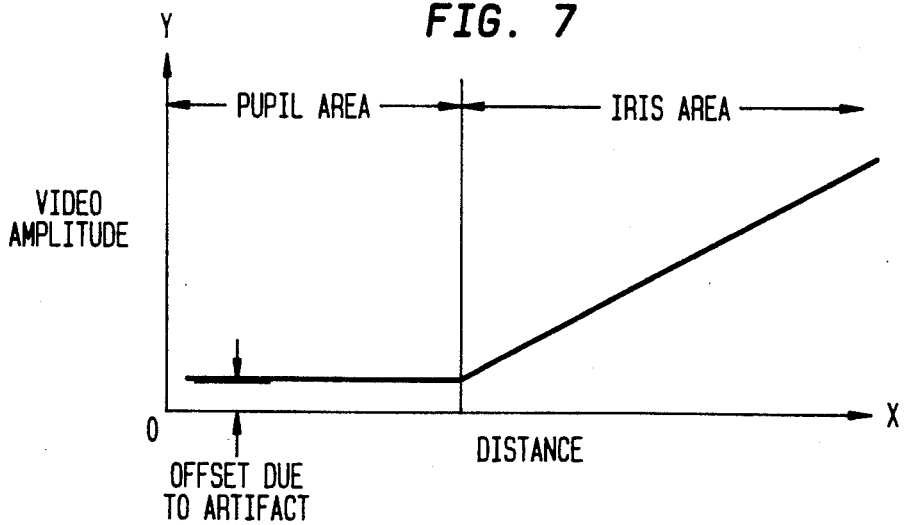
FIG. 7 depicts the filtered data showing the greatest rate of change along the expected distances.

FIG. 7 is a graph of the filtered data showing the greatest rate of change along the expected distances. The point at which the rate of change is greatest is seen where the graph changes path. This location is that which is stored in an array for later plotting as described above.

What is claimed is:

1. The method of determining the perimeter of the pupil in a video display of corneal topography comprising the steps of:
   a. radially scanning the video image of the cornea;
   b. low-pass filtering the video image to obtain the video background illumination level; and
   c. identifying a point on the pupil perimeter by determining the point in each radial scan where said video background undergoes the greatest rate of change in illumination level.

2. The method of claim 1 wherein said identifying is performed utilizing a scanning window for analyzing said video image over a radial range corresponding to the expected range of pupil location.

3. The method of claim 2 wherein said point at which said greatest rate of change is identified is stored in an array according to the sequential number of said radial scan.

4. The method of claim 2, wherein said identifying compares the rates of changes of illumination intensity of adjoining pixel positions to indicate a point on the pupil outline when said comparing of said rates of change changes sign.

5. The method of displaying the perimeter of the pupil upon a color map of the corneal topography comprising the steps of:
   a. obtaining a two-dimensional video image of the cornea;
   b. digitizing the video image to obtain digitized data;
   c. radially scanning the digitized data to create a color map displaying the corneal topography;
   d. identifying a point on each can corresponding to the location of a point on the perimeter of the pupil underlying said cornea, said identifying including determining the point at which the greatest rate of change of illumination intensity occurs; and
   e. superimposing on said color map the succession of said identified pins to form the pupil outline.

* * * * *